(12) United States Patent
Minai

(10) Patent No.: US 8,692,869 B2
(45) Date of Patent: Apr. 8, 2014

(54) IMAGE PROCESSING DEVICE, IMAGE PROCESSING METHOD, MACHINE READABLE RECORDING MEDIUM, ENDOSCOPE SYSTEM

(75) Inventor: Tetsuo Minai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/553,917

(22) Filed: Jul. 20, 2012

(65) Prior Publication Data
US 2013/0113905 A1 May 9, 2013

Related U.S. Application Data

(63) Continuation of application No. PCT/JP2011/079066, filed on Dec. 15, 2011.

(30) Foreign Application Priority Data

Jan. 20, 2011 (JP) ................................. 2011-009972

(51) Int. Cl.
H04N 13/00 (2006.01)

(52) U.S. Cl.
USPC .................... 348/45; 348/65; 348/68; 348/77

(58) Field of Classification Search
USPC ..................................... 348/48, 65, 66, 68, 77
See application file for complete search history.

(56) References Cited

U.S. PATENT DOCUMENTS

| 6,597,390 | B1 * | 7/2003 | Higuchi ........................... 348/65 |
| 2009/0147999 | A1 * | 6/2009 | Maeda et al. ................. 382/106 |
| 2009/0207241 | A1 | 8/2009 | Igarashi et al. |
| 2009/0322863 | A1 | 12/2009 | Takahashi |

FOREIGN PATENT DOCUMENTS

| JP | 2003-265405 A | 9/2003 |
| JP | 2003-290131 A | 10/2003 |
| JP | 2008-229025 A | 10/2008 |
| JP | 2010-5095 A | 1/2010 |
| WO | WO 2007/139187 A1 | 12/2007 |

OTHER PUBLICATIONS

International Search Report dated Feb. 7, 2012 issued in PCT/JP2011/079066.

* cited by examiner

*Primary Examiner* — Sath V Perungavoor
*Assistant Examiner* — Nathnael Aynalem
(74) *Attorney, Agent, or Firm* — Scully, Scott, Murphy & Presser, P.C.

(57) ABSTRACT

An image processing device for processing image information including light reception value information obtained by imaging an inside of a living body includes: a distance information obtainment unit that obtains, at a bright region in the image information, information on a distance to a surface of the living body on the basis of the light reception value information on light in a first wavelength range, and obtains, at a dark region in the image information, information on a distance to the surface of the living body on the basis of the light reception value information on light in a second wavelength range which is a longer wavelength range than the first wavelength range.

10 Claims, 8 Drawing Sheets

IMAGE PROCESSING DEVICE, IMAGE PROCESSING METHOD, MACHINE READABLE RECORDING MEDIUM, ENDOSCOPE SYSTEM

CROSS REFERENCES TO RELATED APPLICATIONS

This application is a continuation of PCT international application Ser. No. PCT/JP2011/079066 filed on Dec. 15, 2011 which designates the United States, incorporated herein by reference, and which claims the benefit of priority from Japanese Patent Applications No. 2011-009972, filed on Jan. 20, 2011, incorporated herein by reference.

BACKGROUND OF THE INVENTION

1. Field of the Invention

The present invention relates to an image processing device that processes an image of the inside of a living body, an image processing method, an image processing program, and an endoscope system.

2. Description of the Related Art

With the advent of capsule endoscopes, which are swallowable endoscopes having an imaging function and a wireless communication function built into a capsule case, endoscope systems, which display images of the inside of an organ (hereinafter referred to as in-vivo images), obtained by a capsule endoscope being introduced into an organ of a subject, have been proposed in the endoscope field. Capsule endoscopes are swallowed by a subject in order to observe the inside of organs of a subject including a patient, then move due to peristaltic motion through the inside of the organs, and are finally excreted out of the body of the subject. The capsule endoscope captures in-vivo images, for example, at an interval of 0.5 seconds during the period of time from being swallowed by the subject to being excreted out of the body of the subject, and sequentially transmits the obtained in-vivo images to the outside using wireless communication.

Each of the in-vivo images transmitted in order of time sequence by the capsule endoscope in this manner using wireless communication is sequentially received by a receiving device outside of the body of the subject. The receiving device stores a group of in-vivo images received from the capsule endoscope in order of time sequence on a storage medium which is inserted in advance. After the groups of in-vivo images obtained by the capsule endoscope have been sufficiently stored, the storage medium in the receiving device is removed from the receiving device, and is inserted into an image display device. The image display device imports the groups of in-vivo images on the inserted storage medium, and sequentially displays each obtained in-vivo image on a display. A user such as a doctor or a nurse observes each in-vivo image displayed sequentially on the image display device, and can observe (inspect) the inside of the organ of the subject through this observation of the in-vivo image.

At this point, to facilitate observation by the user of polyp, lesions, ulcers, or the like, endoscope systems have been proposed which generate and display an image showing a protrusion portion and depression part on the surface of biological tissue, based on the image imaged by the capsule endoscope (for example, refer to Japanese Laid-open Patent Publication No. 2003-265405). With the endoscope system, two images are obtained by causing a capsule endoscope to operate two illumination units during separate periods using a capsule endoscope in which two illumination units are provided at different positions. Then, with the endoscope system, a distance of the surface of biological tissue from the capsule endoscope is calculated by processing the two images using a distance difference between the two illuminations which are at different positions. The endoscope system generates, on the basis of a calculation result, an image including three-dimensional information stereoscopically showing a protrusion portion and a depression part on the surface of biological tissue, or surface orientation information.

SUMMARY OF THE INVENTION

According to an aspect of the present invention, there is provided an image processing device for processing image information including light reception value information obtained by imaging an inside of a living body, the image processing device including: a distance information obtainment unit that obtains, at a bright region in the image information, information on a distance to a surface of the living body on the basis of the light reception value information on light in a first wavelength range, and obtains, at a dark region in the image information, information on a distance to the surface of the living body on the basis of the light reception value information on light in a second wavelength range which is a longer wavelength range than the first wavelength range.

The above and features and advantages of this invention will be understood by reading the following detailed description of, when considered in connection with the accompanying drawings.

DETAILED DESCRIPTION OF THE PREFERRED EMBODIMENTS

Figure 1:
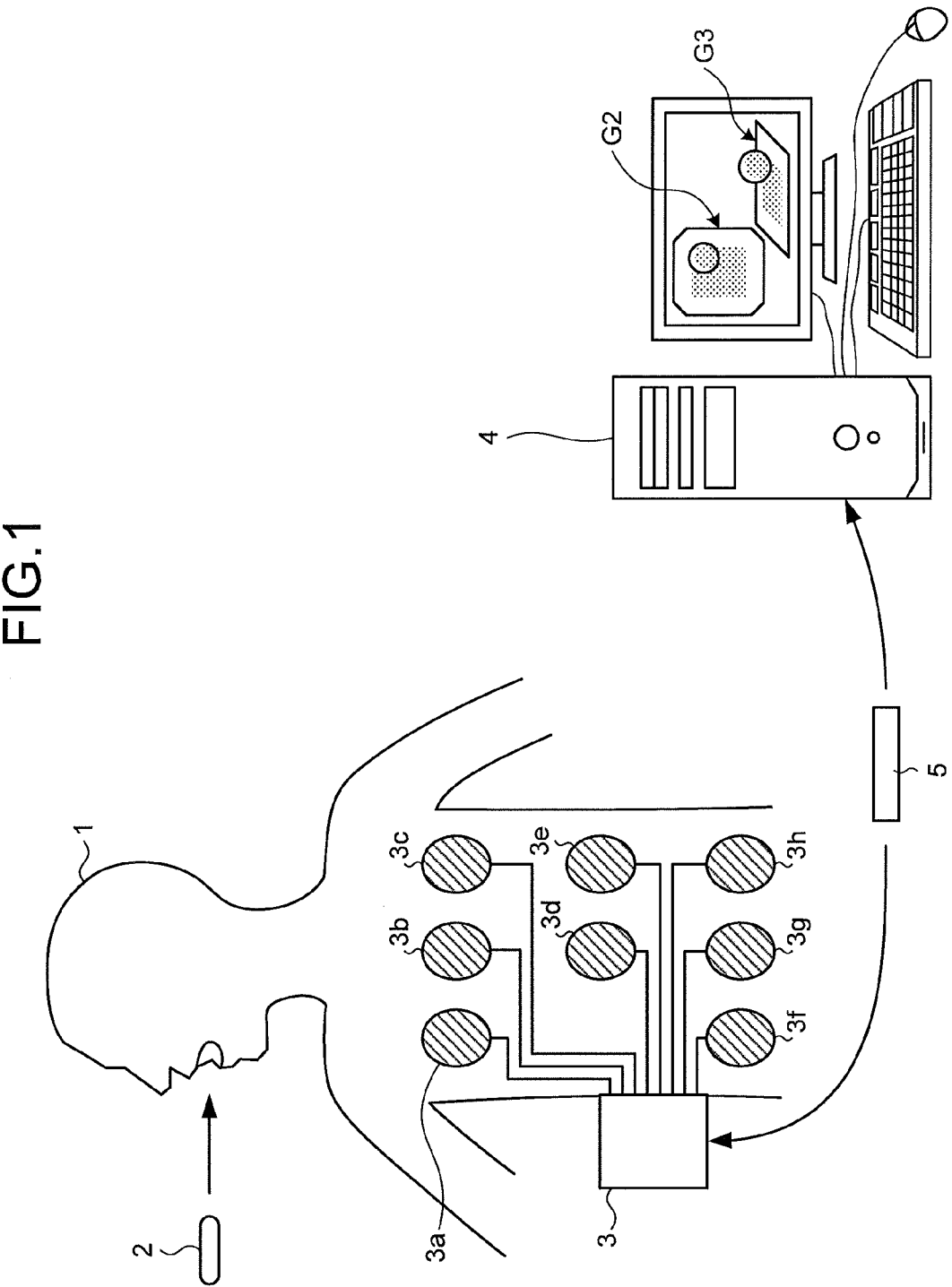
FIG. 1 is a schematic diagram illustrating an configuration example of an endoscope system according an embodiment.

Embodiments of an image processing device, an image processing method, an image processing program, and an endoscope system, according to the present invention are described below in detail referring to drawings. A capsule endoscope is described below as an example of an endoscope device in the endoscope system according to the present invention, but the present invention is not limited to the embodiments. Furthermore, in the description of the drawings, like parts are given like reference numerals.

Embodiments

FIG. 1 is a schematic diagram illustrating a configuration example of an endoscope system according to an embodiment of the present invention. As illustrated in FIG. 1, the endoscope system according to the embodiment includes a capsule endoscope 2 that captures a group of in-vivo images of a subject 1, a receiving device 3 that receives an image signal transmitted wirelessly by the capsule endoscope 2, a workstation 4 that displays the group of in-vivo images imaged by the capsule endoscope 2, and a portable-type storage medium 5 for transferring data between the receiving device 3 and the workstation 4.

The capsule endoscope 2 is an example of an endoscope device that captures an in-vivo image of the subject 1, and has an illumination unit, an imaging element, and a wireless communication unit inside a capsule case. The imaging element is configured by, for example, a CCD sensor in which each pixel is arranged in a matrix in a state where R, G, and B pixels are defined as one set, and by a drive circuit of the CCD sensor. From each pixel of the CCD sensor, a light reception value is output. An R pixel receives light in a wavelength range of 580 nm to 750 nm using an R filter. A G pixel receives light in a wavelength range of 500 nm to 580 nm using a G filter. A B pixel receives light in a wavelength range of 400 nm to 500 nm using a B filter.

The capsule endoscope 2 is introduced into an inside of an organ of the subject 1 by, for example, swallowing, then continues to move due to the peristaltic motion inside of the organ of the subject 1 and sequentially images in-vivo images of the subject 1 at a predetermined interval (for example, an interval of 0.5 seconds). The capsule endoscope 2 illuminates objects inside the organ with illumination light such as white light, and captures the images of the objects illuminated with the illumination light, that is, the in-vivo images of the subject 1. The capsule endoscope 2 transmits image signals of the in-vivo image of the subject 1 thus imaged to an outside receiving device 3 wirelessly, with the imaging time of the in-vivo image and an exposure time data on the in-vivo image being associated with the image signal. The light reception value of each pixel of the CCD sensor built into the capsule endoscope 2 is included in the image signal, and each light reception value is associated with the position information of each corresponding pixel. The capsule endoscope 2 sequentially repeats an operation of capturing the in-vivo image and a wireless transmission operation during the period of time from being introduced into the inside of the organ of the subject 1 to being excreted from the subject 1. Furthermore, since the image-capturing is performed in a state where light from the outside is not incident, in a case where an in-vivo image is imaged in the endoscope system, an emission time of the illumination unit of the capsule endoscope 2 can be considered to be an exposure time.

The receiving device 3 includes a plurality of reception antennas 3a to 3h which are dispersively arranged, for example, on the body surface of the subject 1 and receive wireless signals from the capsule endoscope 2 inside the subject 1 through at least one of the reception antennas 3a to 3h. The receiving device 3 extracts an image signal of each of RGB from the wireless signal from the capsule endoscope 2, and obtains image data on the in-vivo image included in the extracted image signal. The receiving device 3 sequentially stores the image on the storage medium 5 which is inserted in advance, when obtaining one frame of an in-vivo image from the capsule endoscope 2. Furthermore, the receiving device 3 associates the imaging time of the in-vivo image and the exposure time data and the like with each image. Incidentally, the reception antennas 3a to 3h of the receiving device 3, as illustrated in FIG. 1, may be arranged on the body surface of the subject 1, or may be arranged on a jacket which is worn by the subject 1. Furthermore, the number of reception antennas of the receiving device 3 may be one or more, and is not limited to eight.

The workstation 4 imports a variety of data such as the group of in-vivo images of the subject 1 via the storage medium 5 and displays the variety of data such as the imported group of in-vivo images. The workstation 4 obtains the variety of data such as the image data on the in-vivo image of the subject 1, by inserting the storage medium 5, removed from the receiving device 3, into the workstation 4 and importing the data stored in the storage medium 5. The workstation 4 displays an obtained in-vivo image G2 on the display. The in-vivo image G2 is a planar image. Additionally, the workstation 4 obtains data on the distance to the surface of the biological tissue from the capsule endoscope 2 by processing the obtained image data, generates a stereoscopic image G3 including three-dimensional information on the basis of the obtained data on the distance, and thus displays the result.

The storage medium 5 is a portable-type record medium for transferring data between the receiving device 3 and the workstation 4 which are described above. The storage medium 5 may be attached to and detached from the receiving device 3 and the workstation 4 and has a structure from which data may be output and on which data may be recorded when inserted into the receiving device 3 and the workstation 4. In a case of being inserted into the receiving device 3, the storage medium 5 records, for example, the group of in-vivo images processed by the receiving device 3 and the time data on each image. On the other hand, in a case where the storage medium 5 removed from the receiving device 3 and is inserted into the workstation 4, data (the group of in-vivo images, and the like) which the storage medium 5 stores is imported into the workstation 4.

Figure 2:
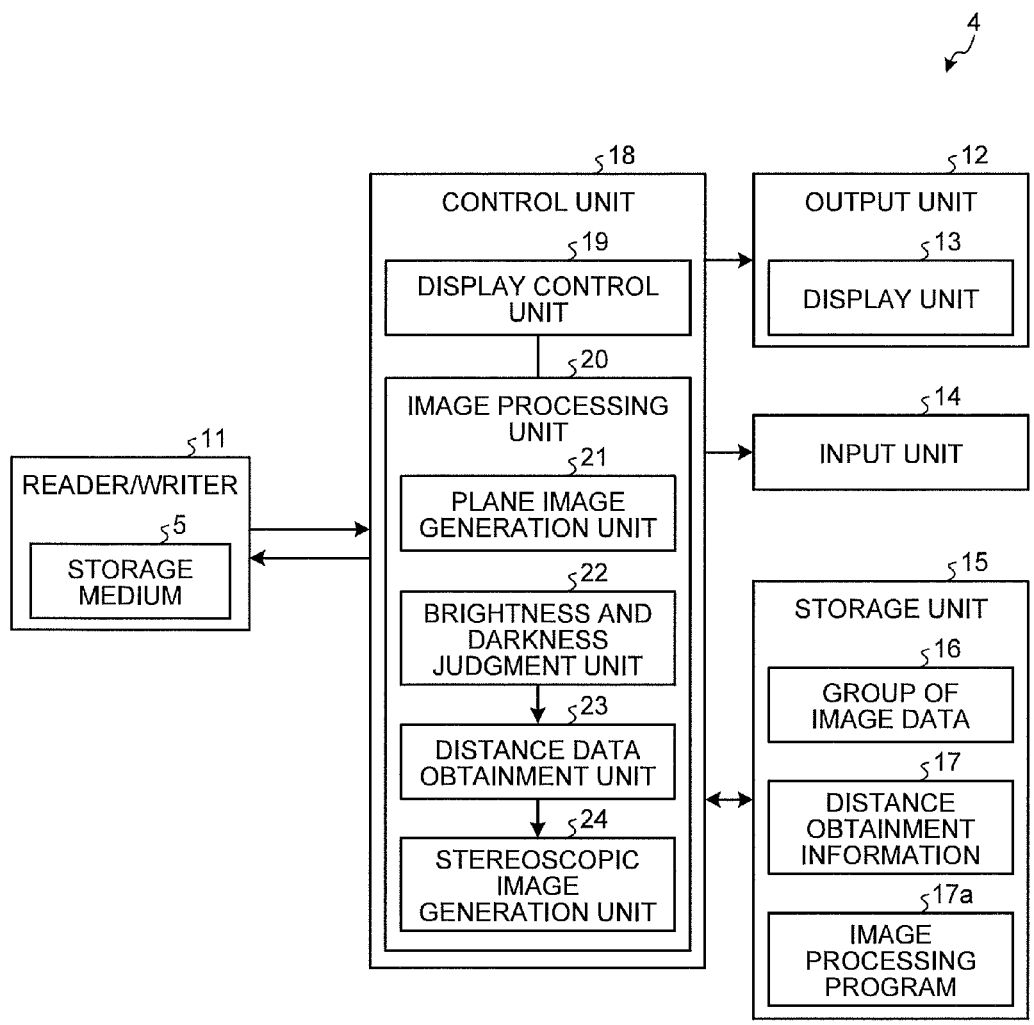
FIG. 2 is a block diagram schematically illustrating a configuration example of a workstation illustrated in FIG. 1.

Next, a configuration of the workstation 4 according to the embodiment of the present invention is described in detail. FIG. 2 is a block diagram schematically illustrating a configuration example of the workstation illustrated in FIG. 1.

As illustrated in FIG. 2, the workstation 4 according to the embodiment includes a reader/writer 11 that imports the data which the storage medium 5 described above stores, an output unit 12 having a display unit 13 which displays the in-vivo image of the subject 1 on a screen, a GUI (Graphical User Interface), and the like, an input unit 14 that inputs a variety of information, a storage unit 15 that stores the data and the like imported by the reader/writer 11, and a control unit 18 that controls each component of the workstation 4.

The storage medium 5 removed from the receiving device 3 is detachably inserted to the reader/writer 11, and the reader/writer 11 imports the data which the storage medium 5 stores and transfers the imported data to the control unit 18. Furthermore, in a case where an initialized storage medium 5 is inserted into the reader/writer 11, the reader/writer 11 may write data, which the control unit 18 instructs to write, onto the storage medium 5. The data which the reader/writer 11 imports from the storage medium 5 is a group 16 of image data items corresponding to the in-vivo image of the subject 1, time data on, for example, the exposure time of each in-vivo image, and the like. On the other hand, the data which the reader/writer 11 writes on the storage medium 5 is, for example, specified data on a patient name specifying the subject 1, a patient ID and the like.

The output unit 12 outputs the information on the in-vivo observation. The display unit 13 is embodied using a display capable of displaying an image, such as a CRT display and a liquid crystal display, and displays a variety of information on the in-vivo image and the like, which the control unit 18 instructs to display.

The input unit 14 is embodied using an input device such as a keyboard and a mouse, and inputs a variety of information to the control unit 18 corresponding to the input manipulation by the user.

The storage unit 15 is embodied using a storage medium such as a RAM, an EEPROM, or a hard disk, stores the variety of data and the like which the control unit 18 instructs to store, and transfers the stored data which the control unit 18 instructs to transfer to the control unit 18. Specifically, the storage unit 15 stores the data which the storage medium 5 stores, imported by the reader/writer 11 described above, that is, the group 16 of image data items on the subject 1 and the exposure time data on each in-vivo image, under the control of the control unit 18. The storage unit 15 reads the in-vivo image, which the control unit 18 instructs to transfer, from the group of in-vivo images and outputs the result to the control unit 18. Furthermore, the storage unit 15 stores a variety of information, which is necessary in a case where distance information is obtained by performing image processing, as distance obtainment information 17.

Furthermore, the storage unit 15 stores an image processing program 17a which instructs a processor provided in the image processing device that processes image information including light reception value information obtained by imaging the inside of the living body, to perform the following.

The control unit 18 controls each operation of the reader/writer 11, the output unit 12, the input unit 14, and the storage unit 15 which are components of the workstation 4 and controls the input and output of signals between the components. The control unit 18 controls the reader/writer 11 in such a manner as to import the data which the storage medium 5 stores, and controls the storage unit 15 in such a manner as to store the imported data (the image data, the exposure time data on each in-vivo image, and the like), on the basis of the instruction information input by the input unit 14. In the control unit 18, memory (not shown) storing the control program configured to control each component is provided, and the control unit 18 reads the program from the memory and controls each component by executing the program. In the program, an image processing program is also provided which causes the workstation 4 to process the image data including the light reception value obtained by imaging the inside of the living body with one-time exposure.

Furthermore, the control unit 18 includes a display control unit 19 and an image processing unit 20. The display control unit 19 controls the image display process performed by the display unit 13, on the basis of the instruction information input by the input unit 14. The image processing unit 20 processes the image of the group 16 of the image data item stored in the storage unit 15, and thus generates a stereoscopic image including the in-vivo image for display and three-dimensional information. The display control unit 19 displays the image generated by the image processing unit 20 on the display unit 13. The image processing unit 20 has a plane image generation unit 21, a brightness and darkness judgment unit 22, a distance data obtainment unit 23, and a stereoscopic image generation unit 24.

The plane image generation unit 21 generates an in-vivo image G2 for display, by obtaining the image data of the display object from the group 16 of image data item in the storage unit 15, performing a variety of adjustments such as WB adjustment, and changing the post-adjustment image data to a format corresponding to a display method in the display unit 13.

The brightness and darkness judgment unit 22 obtains the image data on the image instructed to be displayed stereoscopically and judges whether each region is a bright region or a dark region, every unit region which is defined as the judgment object, on the basis of the light reception value information on each pixel, included in the image data. The brightness and darkness judgment unit 22 performs a judgment process for, for example, a pixel region that includes R, G, and B pixels positioned adjacent to each other as one unit.

The distance data obtainment unit 23 obtains the data on the distance to the surface of the living body by processing image data corresponding to one in-vivo image. That is, the distance data obtainment unit 23 processes the image data including the light reception value information obtained by imaging the inside of the living body with one-time exposure. Similarly to the brightness and darkness judgment unit 22, the distance data obtainment unit 23 performs a distance data obtainment process for, for example, each of a pixel region that includes R, G, and B pixels positioned adjacent to each other as one unit.

The distance data obtainment unit 23 obtains the data on the distance to the surface of the living body, for each region in the image data on one image of the processing object, referring to the distance obtainment information 17 stored in the storage unit 15. At this point, in the pixel of the CCD sensor, the light reception amounts are different from each other according to the distance of the surface of the living body from the capsule endoscope 2 emitting light. Thus, the storage unit 15 stores a relation in which each light reception value of the pixel is associated with the distance to the surface of the living body, as the distance obtainment information 17. Furthermore, the light reception values are different in the pixel from each other according to the exposure time even though the distance to the surface of the living body is the same. Thus, the relation in which each light reception value of the pixel is associated with the distance to the surface of the living body is established according to each exposure time and is stored in the storage unit 15. Furthermore, light sensitivities and spectral characteristics are different from each other, by the R, G, and B pixels, and scattering characteristics on the surface of the living body are different from each other, by red light, green light, and blue light. Thus, the relation in which each light reception value of the pixel associated with the distance to the surface is established for each of R, G, and B pixels and is stored in the storage unit 15. The distance data obtainment unit 23 obtains the data on the distance to the surface of the living body, referring to any one of pieces of the distance obtainment information 17 stored in the storage unit 15. Furthermore, the relation between the light reception value of each pixel and each distance to the surface of the living body may be for example, a function showing a relation between the light reception value of the pixel and the distance to the surface of the living body, or may be a correspondence table which maps the light reception value of each of R and G pixels onto each distance to the surface of the living body.

In the bright region among the image data, the distance data obtainment unit 23 obtains the data on the distance to the surface of the living body, on the basis of the light reception value information on the light in a first wavelength range and the exposure time. Specifically, in the bright region, the distance data obtainment unit 23 obtains the data on the distance to the surface of the living body, on the basis of the light reception value information on the B pixel which receives blue light included in the wavelength range smaller than 500 nm, which is a shorter wavelength range than the R and G pixels, and the exposure time data at the time of imaging an image of the processing object. In this case, the distance data obtainment unit 23 refers to the relation in which each light reception value of the B pixel corresponding to the exposure time in the image is associated with each distance to the surface of the living body, among the distance obtainment information 17 stored in the storage unit 15. Furthermore, since spectral characteristics between red light, green light, and blue light, light sensitivity of the CCD sensor and the scattering characteristic on the surface of biological tissue are different from each other, the distance data obtainment unit 23 may obtain the distance data, using a value which is a result of compensating the light reception value on the basis of these characteristics.

In the dark region among the image data, the distance data obtainment unit 23 obtains the information on the distance to the surface of the living body, on the basis of the light reception value information on the light in a second wavelength range, which is a longer wavelength range than the first wavelength range, and the exposure time. Specifically, in the dark region among the image data, the distance data obtainment unit 23 obtains data on the distance to the surface of the living body, on the basis of the light reception value data on the R pixel receiving red light and the light reception value data on the G pixel receiving green light included in the wavelength range equal to or more than 500 nm which is a longer wavelength range than the B pixel, and the exposure time data at the time of imaging the processing object. In this case, the distance data obtainment unit 23 refers to the relation in which each light reception value of the R pixel corresponding to the exposure time in the image is associated with each distance to the surface of the living body, and the relation in which each light reception value of the G pixel is associated with each distance to the surface of the living body, among the distance obtainment information 17 stored in the storage unit 15. Incidentally, the bright region and the dark region in the image data are judged in advance by the brightness and darkness judgment unit 22 immediately prior to the distance data obtainment by the distance data obtainment unit 23.

The stereoscopic image generation unit 24 generates the stereoscopic image including three-dimensional information, on the basis of the data on each distance to the living body, obtained by the distance data obtainment unit 23 for each region of the image data on one image. The stereoscopic image generation unit 24 generates, as a stereoscopic image including three-dimensional information, the stereoscopic image G3 illustrated in FIG. 1, in which the biological tissue expressed in the in-vivo image G2 is viewed from the front, upper lateral side. Of course, not limited to this, the stereoscopic image generation unit 24 may generate a side view or a cross-sectional view of the biological tissue expressed in the in-vivo image G2. The display unit 13 displays the in-vivo image which is the plane image generated by the plane image generation unit 21 and the stereoscopic image generated by the stereoscopic image generation unit 24, under the control of the display control unit 19.

Figure 3:
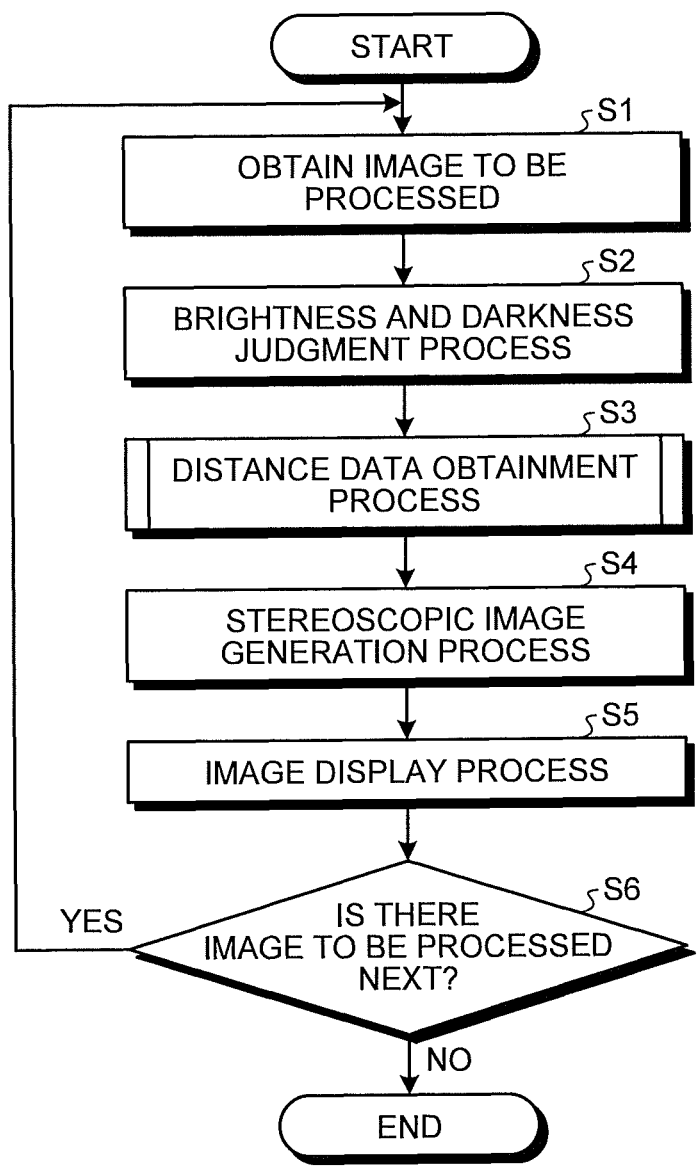
FIG. 3 is a flowchart illustrating a process procedure for an image processing method in the workstation illustrated in FIG. 2.

Next, the image processing in the workstation 4 is described referring to FIG. 3. FIG. 3 is a flowchart illustrating a process procedure for an image processing method in the workstation illustrated in FIG. 2.

As illustrated in FIG. 3, in the workstation 4, when the instruction information on the instruction to display stereoscopically is input from the input unit 14, the image processing unit 20 selects the image data on one plane image which is a processing object which is instructed to be displayed stereoscopically in the instruction information, from among the group 16 of image data items stored by the storage unit 15 and obtains the result (Step S1).

Subsequently, the brightness and darkness judgment unit 22 obtains the image data on the image which is instructed to be displayed stereoscopically and performs a brightness and darkness judgment process to judge whether each region is the bright region or the dark region, every unit area which is defined as the judgment object, on the basis of the light reception value information on each pixel, included in the image data (Step S2). The result of the judgment by the brightness and darkness judgment unit 22 is associated with each region of each image data.

At this time, in a case where the light reception value of the R pixel receiving red light in the longer wavelength range than the G and B pixels exceeds a predetermined threshold in the set of the R, G, and B pixels as the judgment object, the brightness and darkness judgment unit 22 judges this pixel region as the bright region. In contrast, in a case where the light reception value of the R pixel is equal to or less than the predetermined threshold, the brightness and darkness judgment unit 22 judges this pixel region as the dark region.

Alternatively, in a case where the light reception value of the G pixel in addition to the light reception value of the R pixel exceed the predetermined threshold in the set of the R, G, and B pixels as the judgment object, the brightness and darkness judgment unit 22 may judge this pixel region as the bright region. In a case where the light reception value of the R pixel and the light reception value of the G pixel are equal to or less than the predetermined threshold, the brightness and darkness judgment unit 22 may judge this pixel region as the dark region.

Alternatively, since the light reception value of the R pixel and the light reception value of the G pixel relatively easily exceed a light reception upper limit of the imaging element to be in a saturated state at the bright region in the image imaged by the capsule endoscope 2, in a case where the light reception value of the G pixel in addition to the light reception value of the R pixel exceed the light reception upper limit to be in the saturated state, the brightness and darkness judgment unit 22 may judge this pixel region as the bright region.

Incidentally, the brightness and darkness judgment process by the brightness and darkness judgment unit 22 may be performed in advance prior to performing a sequence of processes illustrated in FIG. 3. In this case, instead of performing the brightness and darkness judgment process (Step S2), the image processing unit 20 may obtain the judgment result corresponding to the image data of the processing object, among the judgment results performed in advance.

Subsequently, the distance data obtainment unit 23 performs the distance data obtainment process (Step S3) to obtain the data on the distance to the surface of the living body in the image data on one image of the processing object, referring to the distance obtainment information 17 stored in the storage unit 15. The distance data obtainment process is performed for each pixel region that includes the R, G, and B pixels positioned adjacent to each other as one unit.

The stereoscopic image generation unit 24 performs the stereoscopic image generation process (Step S4) for generating the stereoscopic image corresponding to the plane image of the processing object, on the basis of each distance data obtained by the distance data obtainment unit 23. Incidentally, the stereoscopic image generation unit 24 generates the stereoscopic image corresponding to the plane image, on the basis of the distance data on each pixel region obtained in the distance data obtainment process. The display control unit 19 perform the image display process to display the stereoscopic image generated by the stereoscopic image generation unit 24 on the display unit 13 (Step S5) In this case, the display control unit 19, as illustrated in FIG. 1, may display the stereoscopic image G3 and the plane image G2 used to generate the stereoscopic image together.

The image processing unit 20 judges whether there is an image to be processed next or not on the basis of the instruction information input from the input unit 14 (Step S6). In a case where it is judged that there is an image to be processed next (Step S6: Yes), the image processing unit 20 returns to Step S1, obtains the next image of the processing object, and performs the image processing. On the one hand, in a case where it is judged that there is no image to be processed next (Step S6: No), the image processing unit 20 ends the image processing.

Figure 4:
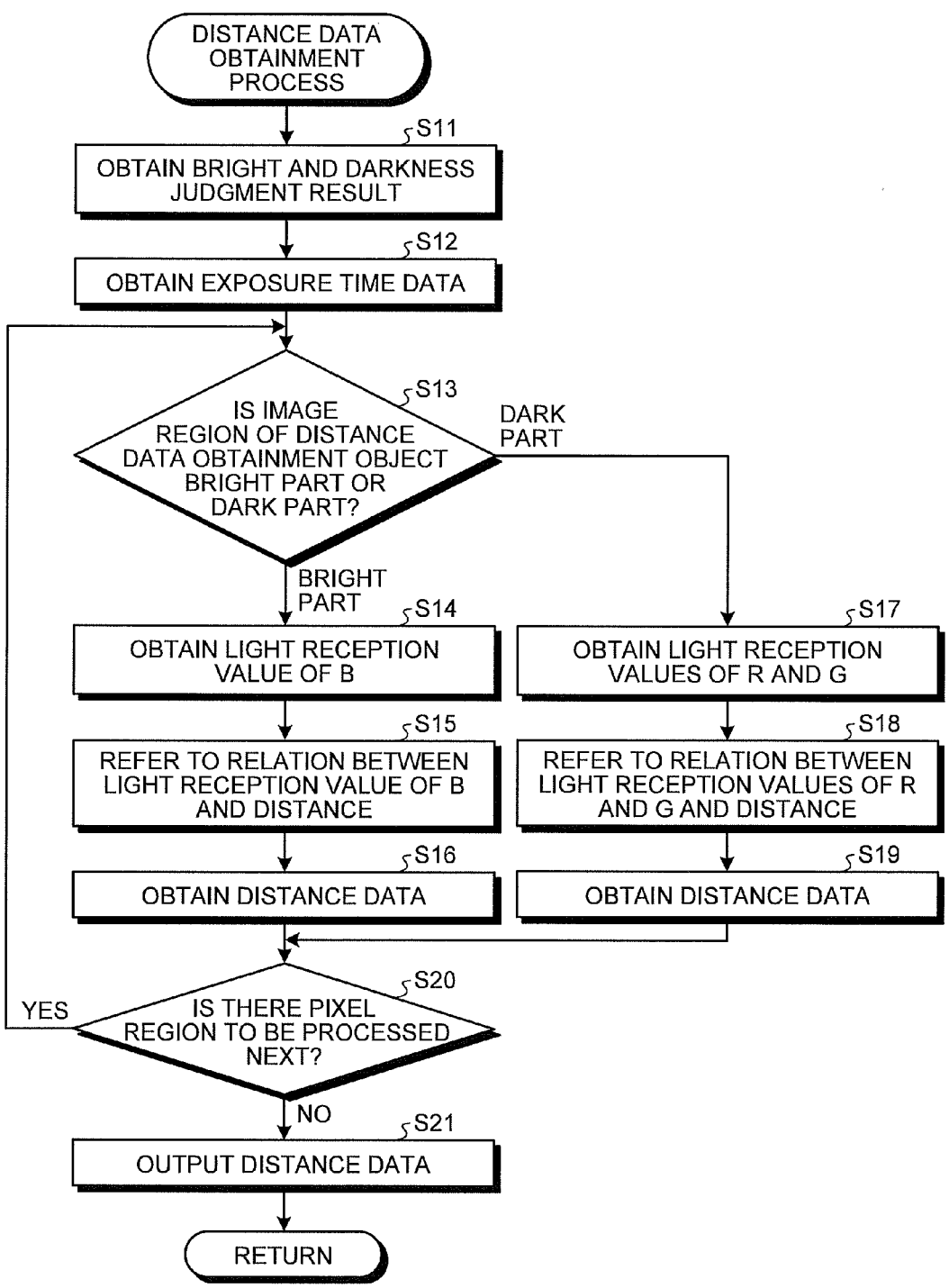
FIG. 4 is a flowchart illustrating a process procedure for a distance data obtainment process illustrated in FIG. 3.

Next, the distance data obtainment process illustrated in FIG. 3 is described referring to FIG. 4. FIG. 4 is a flowchart illustrating the process procedure for a distance data obtainment process illustrated in FIG. 3. As illustrated in FIG. 4, the distance data obtainment unit 23 obtains a brightness and darkness judgment result corresponding to the image data of the processing object, produced by the brightness and darkness judgment unit 22 (Step S11). Subsequently, the distance data obtainment unit 23 obtains the exposure time data in the image data of the processing object (Step S12). The distance data obtainment unit 23 judges whether the pixel region of the distance data obtainment object is the bright part or the dark part on the basis of the obtained brightness and darkness judgment result (Step S13).

Figure 5:
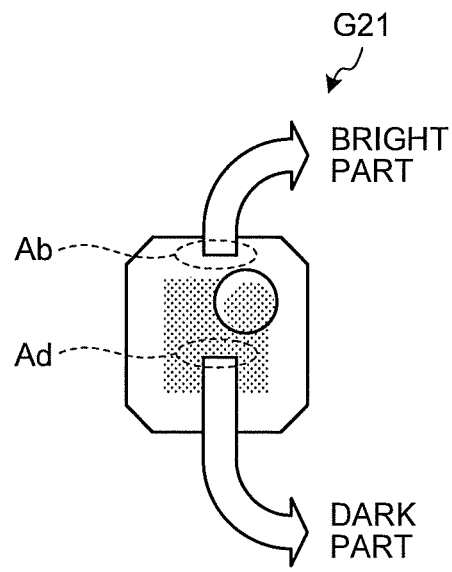
FIG. 5 is a view illustrating an example of an in-vivo image displayed on a display screen of a display unit illustrated in FIG. 2.
Figure 6:
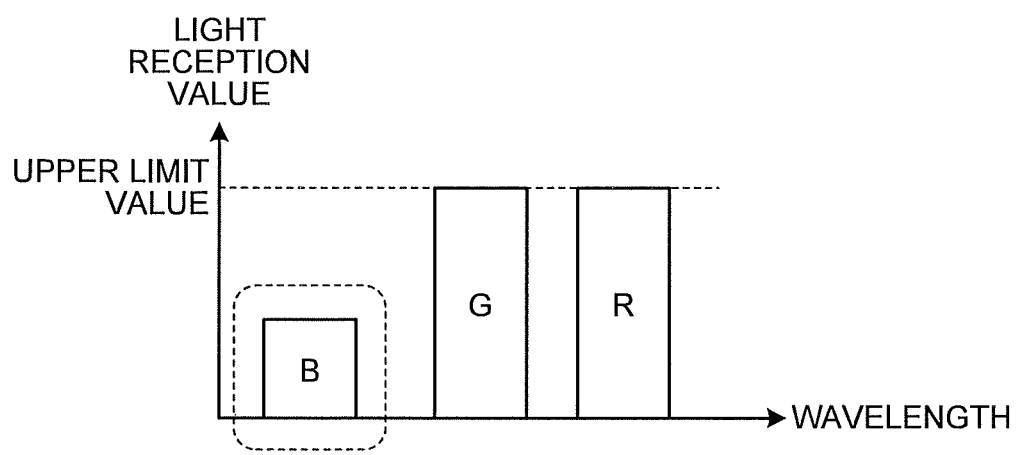
FIG. 6 is a view schematically illustrating the dependence of a light reception value on a wavelength in a bright region.

In a case where the pixel region of the distance data obtainment object is judged as the bright part (Step S13: the bright part), the distance data obtainment unit 23 obtains the light reception value data on the B pixel in this pixel region (Step S14). At this point, FIG. 6 is a view schematically illustrating the dependence of the light reception value on the wavelength in the bright region. Because the biological tissue has spectral sensitivity characteristics which mostly reflects the long wavelength component, for example, in a region Ab which is judged as the bright part in the plane image G21 illustrated in FIG. 5, all of the light reception value of the R pixel and the light reception value of the G pixel often exceed the light reception upper limit value of the imaging element and thus are in a saturated state, as illustrated in FIG. 6. Thus, in the bright region, since the exact light reception value of the R pixel and the exact light reception value of the G pixel may be not obtained, it is difficult to obtain the exact distance to the surface of the biological tissue using the light reception value of the R pixel and the light reception value of the G pixel. In contrast, as illustrated in FIG. 6, the light reception value of the B pixel, even though it is in the bright region, is less than the upper limit value most of the time. Accordingly, the distance data obtainment unit 23 obtains the distance data using the light reception value of the B pixel showing the exact value, not the light reception values of the G and R pixels which exceed the light reception upper limit value of the imaging element and are in a saturated state, in the image region judged as the bright region.

The distance data obtainment unit 23 refers to the relation between each light reception value of the B pixel and each distance to the surface of the living body, among the distance obtainment information 17 stored in the storage unit 15 (Step S15). Each light reception value of the B pixel and each distance to the surface of the living body have, for example, relations illustrated by curved lines Lb1 to Lb3, in FIG. 7. The curved lines Lb1 to Lb3 correspond to different exposure time, respectively, and the exposure time becomes longer in this order of the curved line Lb1, the curved line Lb2, and the curved line Lb3.

Figure 7:
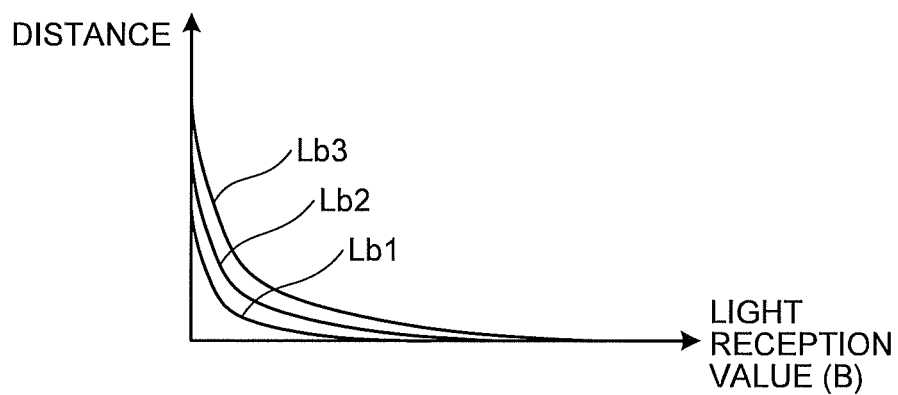
FIG. 7 is a view illustrating the relation between each light reception value of a B pixel and each distance to the surface of the living body.

The distance data obtainment unit 23 refers to the curved line corresponding to the exposure time of the image data of the processing object, among the curved lines Lb1 to Lb3 illustrated in FIG. 7. And, the distance data obtainment unit 23 obtains the distance data corresponding to the light reception value of the B pixel in the pixel region of the processing object, on the basis of the referred relation between each light reception value of the B pixel and each distance to the surface of the living body (Step S16).

Figure 8:
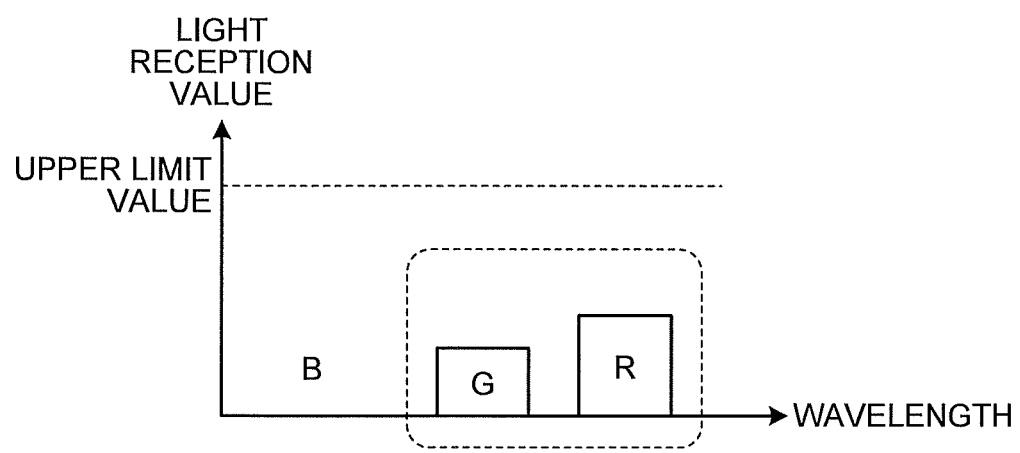
FIG. 8 is a view schematically illustrating the dependence of a light reception value on a wavelength in a dark region of image data.

On the other hand, in Step S13, in a case where the pixel region of the distance data obtainment object is judged as the dark part (Step S13: the dark part), the distance data obtainment unit 23 obtains the light reception value data on the R pixel and the G pixel in this pixel region (Step S17). At this point, FIG. 8 is a view schematically illustrating the dependence of the light reception value on the wavelength in the dark region. Because it is easy for wavelength components of the short wavelength to be scattered on the surface of the biological tissue, for example, in the region Ad which is judged as the dark part in the plane image G21 illustrated in FIG. 5, the closer the light reception value of the B pixel is to almost zero, the more often the value is extremely small, as illustrated in FIG. 8. In contrast, since the biological tissue has the spectral sensitivity characteristics which mostly reflects the long wavelength component, the light reception values of the R pixel and the G pixel, even though they are in the dark region, are often at the level which is processable to a certain degree. Accordingly, in the dark region, the distance data are obtained, using the light reception values of the R pixel and the G pixel from which the light reception value at the level which is processable to a certain degree may be detected, not the light reception value of the B pixel which is at an almost zero level.

The distance data obtainment unit 23 refers to the relation between each light reception value of the R pixel and the G pixel, and each distance to the surface of the living body, among the distance obtainment information 17 stored in the storage unit 15 (Step S18). Each light reception value of the R pixel and each distance to the surface of the living body have, for example, relations indicated by curved lines Lr1 to Lr3 in FIG. 9. The curved lines Lr1 to Lr3 correspond to different exposure time, respectively, and the exposure time becomes longer in this order of the curved line Lr1, the curved line Lr2, and the curved line Lr3. Furthermore, each light reception value of the G pixel and each distance to the surface of the living body have, for example, relations indicated by curved lines Lg1 to Lg3, in FIG. 10. The curved lines Lg1 to Lg3 correspond to different exposure time, respectively, and the exposure time becomes longer in this order of the curved line Lg1, the curved line Lg2, and the curved line Lg3.

Figure 9:
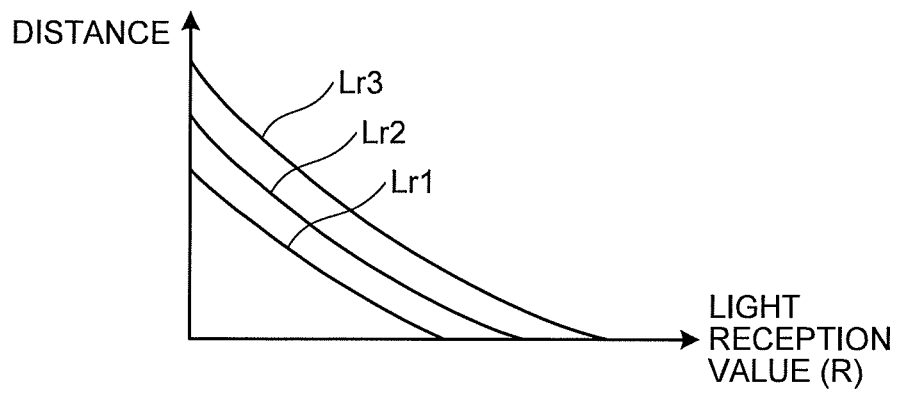
FIG. 9 is a view illustrating the relation between each light reception value of an R pixel and each distance to the surface of the living body.
Figure 10:
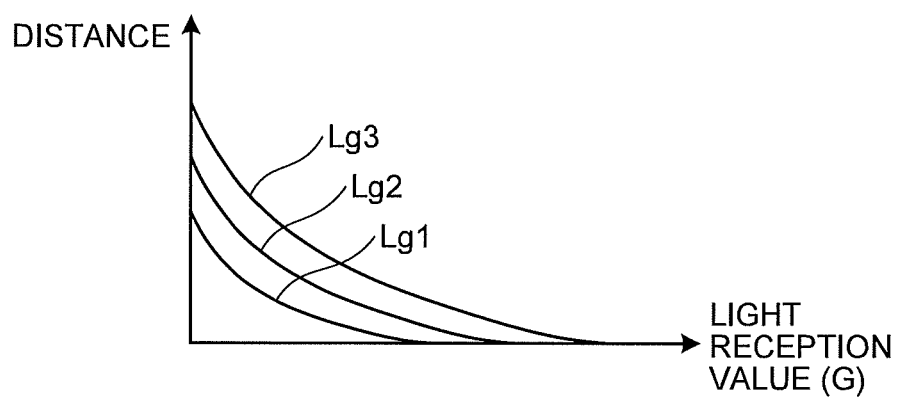
FIG. 10 is a view illustrating the relation between each light reception value of a G pixel and each distance to the surface of the living body.

The distance data obtainment unit 23 refers to the curved line corresponding to the exposure time of the image data of the processing object, among the curved lines Lr1 to Lr3 illustrated in FIG. 9 and the curved lines Lg1 to Lg3 illustrated in FIG. 10. And, the distance data obtainment unit 23 obtains the distance data corresponding to the light reception value of the B pixel in the pixel region of the processing object, on the basis of the referred relation between each light reception value of the R pixel and G pixel and each distance to the surface of the living body (Step S19). For example, the distance data obtainment unit 23 individually obtains the distance data on each of the R pixel and the G pixel, and obtains an average value of the distance based on the light reception value of the R pixel and the distance based on the light reception value of the G pixel, as the distance in the pixel region of the processing object. Alternatively, the distance data obtainment unit 23 may obtain the distance in the pixel region of the processing object by combining each value which is a result of performing predetermined weighting on each of the distance based on the light reception value of the R pixel and the distance based on the light reception value of the G pixel.

Figure 11:
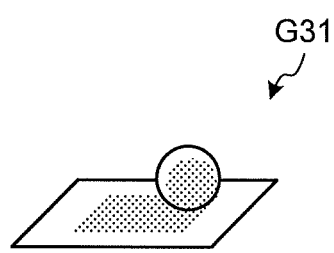
FIG. 11 is a view illustrating an example of an image which a stereoscopic image generation unit illustrated in FIG. 2 generates.

Subsequently, the distance data obtainment unit 23 judges whether there is a pixel region to be processed next or not (Step S20). In a case (Step S20: Yes) where it is judged that there is a pixel region to be processed next, the distance data obtainment unit 23 returns to Step S13 and performs the distance data obtainment process on the next pixel region of the processing object. On the other e hand, in a case (Step S20: No) where it is judged that there is not pixel region to be processed next, the distance data obtainment unit 23 outputs the distance data relating to the image data of the processing object in a state in which the distance data is associated with the position information on each pixel region (Step S21) and ends the distance data obtainment process. Furthermore, in the stereoscopic image generation process (Step S4) illustrated in FIG. 3, a stereoscopic image G31 (FIG. 11) corresponding to the plane image G21 is generated, on the basis of the distance data on each pixel region.

As described above, in the embodiment, the image data obtained by the exposure with one-time illumination is used. Furthermore, the light reception value data on the B pixel showing the light reception value which is less than the light reception upper limit is used in the bright region, and the light reception value data on the R pixel and the G pixel showing the light reception values which are processable is used in the dark region. Therefore, according to the embodiment, there is an effect that by properly distinguishing the light reception value data to be used in the bright region and the dark region, the distance to the surface of the biological tissue can be stabilized and be precisely obtained, avoiding the influence of the spectral sensitivity characteristics of the biological tissue, on the basis of the image data obtained by the expose with one-time illumination. Especially, in a case where the capsule endoscope is used, a sense of distance is difficult to feel and additionally abnormal region may not be observed from a predetermined angle of view, since the body of the endoscope moves inside the organ of the subject 1, for example, owing to the peristaltic motion inside of the body without being moved by the operator's manipulation. However, according to the embodiment, since the distance to the surface of the biological tissue can be stabilized and obtained, the image including the adequate three-dimensional information can be generated and the smooth observation can be done.

Figure 12:
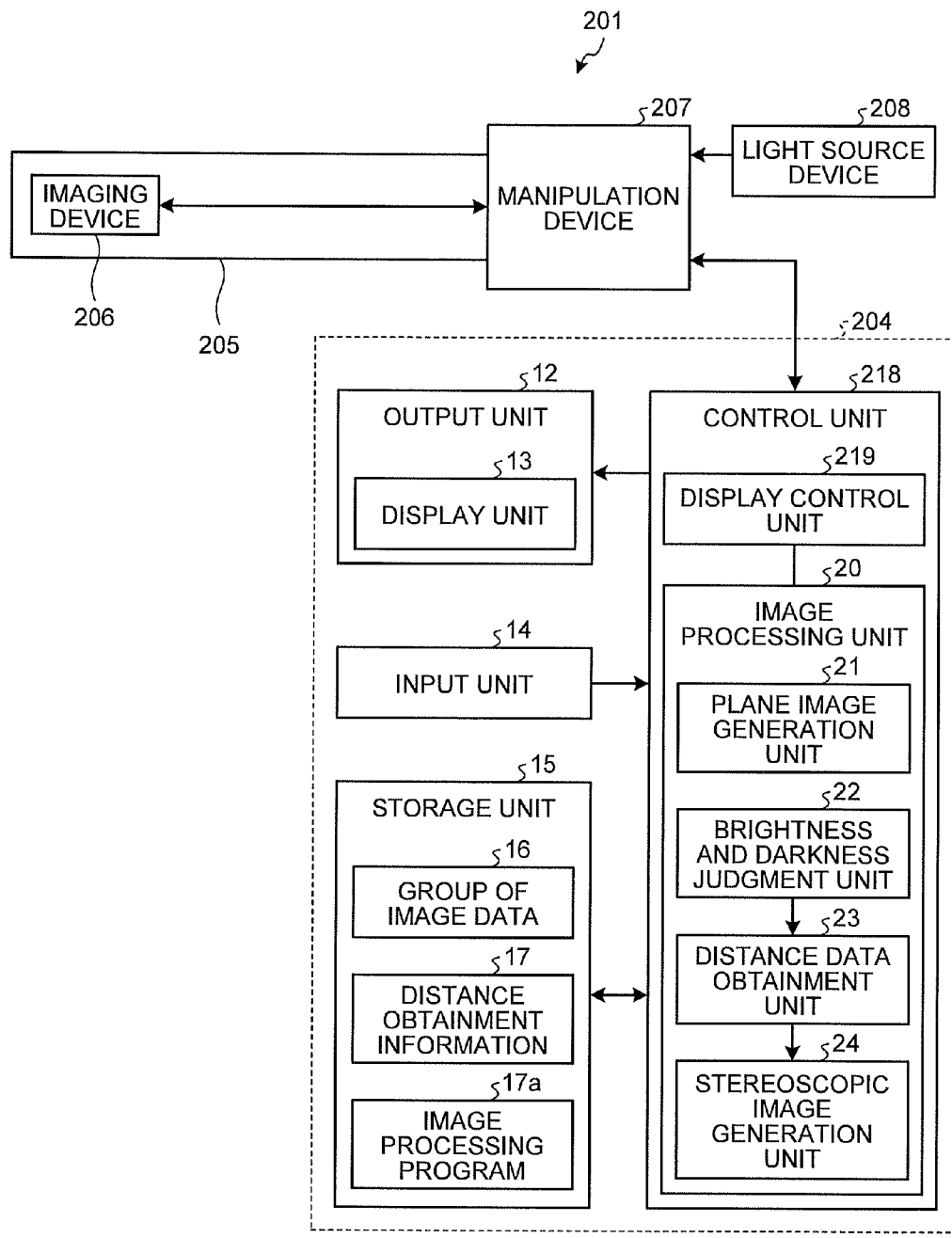
FIG. 12 is a diagram illustrating another configuration of the endoscope system according to the embodiment.

Furthermore, in the embodiment, the endoscope system using the capsule endoscope is described as an example, but, of course, is not limited to this. As illustrated in FIG. 12, the endoscope system may be applied to an endoscope system which inserts into the body an elongated-shaped insertion unit 205 on the tip of which an imaging device 206 that images the in-vivo image is mounted.

This endoscope system 201 has a manipulation device 207 for manipulating the insertion unit 205 and the imaging device 206, a light source device 208 for illuminating an imaging field of view of the imaging device 206, a workstation 204 for generating an endoscope image on the basis of image data imaged by the imaging device 206. Similarly to the workstation 4 illustrated in FIG. 2, the workstation 204 has an output unit 12 which has a display unit 13, an input unit 14, a storage unit 15, and a control unit 218 having a display control unit 219 controlling an image display process by the display unit 13 to display image data imaged by the imaging device 206 and an image processing unit 20.

Even in the endoscope system 201 illustrated in FIG. 12, by properly distinguishing the light reception value data to be used in the bright region and the dark region, the distance to the surface of the biological tissue can be stabilized and obtained precisely, on the basis of the image data obtained by the expose with one-time illumination.

As described above, the image processing device according to the present invention, the image processing method, the image processing program and the endoscope system are suitable for stabilizing the distance to the surface of the biological tissue and precisely obtaining the distance, in the capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device for processing image information including light reception value information obtained by imaging an inside of a living body with one-time exposure, the image processing device comprising:
    a distance information obtainment unit that obtains, at a bright region in the image information, information on a distance to a surface of the living body on the basis of exposure time and the light reception value information on light in a first wavelength range, and obtains, at a dark region in the image information, information on a distance to the surface of the living body on the basis of exposure time and the light reception value information on light in a second wavelength range which is a longer wavelength range than the first wavelength range.

2. The image processing device according to claim 1, further comprising an image generation unit that generates an image including three-dimensional information on the basis of the information on the distance to the living body obtained by the distance information obtainment unit.

3. The image processing device according to claim 2, further comprising a display unit that displays the image including three-dimensional information generated by the image generation unit.

4. The image processing device according to claim 1, further comprising a brightness and darkness judgment unit that judges whether each region of a judgment object is either the bright region or the dark region on the basis of the light reception value information included in the image information.

5. The image processing device according to claim 4, wherein the brightness and darkness judgment unit judges that a region of the judgment object is the bright region in a case where the light reception value of the light in the second wavelength range exceeds a predetermined threshold in the region of the judgment object, and judges that the region of the judgment object is the dark region in a case where the light reception value of the light in the second wavelength range is equal to or less than the predetermined threshold in the region of the judgment object.

6. The image processing device according to claim 1, wherein the first wavelength range is less than 500 nm and the second wavelength range is equal to or more than 500 nm.

7. An operating method of an image processing device for processing image information including light reception value information obtained by imaging an inside of a living body with one-time exposure, the method comprising:
 causing a distance information obtainment unit to obtain, at a bright region in the image information, information on a distance to a surface of the living body on the basis of exposure time and the light reception value information on light in a first wavelength range and to obtain, at a dark region in the image information, information on a distance to the surface of the living body on the basis of exposure time and the light reception value information on light in a second wavelength range which is a longer wavelength range than the first wavelength range.

8. A non-transitory computer-readable storage medium with an executable image processing program stored thereon, wherein the program instructs a processor in an image processing device, for image information including light reception value information obtained by imaging an inside of a living body with one-time exposure, to perform:
 obtaining, at a bright region in the image information, information on a distance to a surface of the living body on the basis of exposure time and the light reception value information on light in a first wavelength range; and
 obtaining, at a dark region in the image information, information on a distance to the surface of the living body on the basis of exposure time and the light reception value information on light in a second wavelength range which is a longer wavelength range than the first wavelength range.

9. An endoscope system comprising:
 an endoscope device configured to be introduced into an inside of a living body and to image the inside of the living body; and
 the image processing device according to claim 1.

10. The endoscope system according to claim 9, wherein the endoscope device is a capsule endoscope.

* * * * *